United States Patent [19]

Hata et al.

[11] Patent Number: 5,348,950
[45] Date of Patent: * Sep. 20, 1994

[54] PLATINUM(II) COMPLEX AND ANTITUMOR AGENT

[75] Inventors: Go Hata, Fujisawa; Tatsuya Kaneko; Hideki Kawai, both of Kamakura; Masato Mutoh, Yokohama; Hideyuki Hashimoto, Otsu, all of Japan

[73] Assignee: Toray Industries, Inc., Japan

[*] Notice: The portion of the term of this patent subsequent to Apr. 12, 2011 has been disclaimed.

[21] Appl. No.: 894,779

[22] Filed: Jun. 5, 1992

[30] Foreign Application Priority Data

Jun. 10, 1991 [JP] Japan .................................. 3-138029

[51] Int. Cl.$^5$ .......................... A61K 33/24; C07F 15/00
[52] U.S. Cl. .................................... 514/186; 514/184; 549/3; 549/210
[58] Field of Search ...................... 549/210, 3; 514/184, 514/186

[56] References Cited

U.S. PATENT DOCUMENTS

| | | | |
|---|---|---|---|
| 4,912,100 | 3/1990 | Ohno et al. | 549/210 |
| 4,980,347 | 12/1990 | Ohno et al. | 549/210 |

FOREIGN PATENT DOCUMENTS

| | | |
|---|---|---|
| 0264109 | 4/1988 | European Pat. Off. |
| 0341318 | 11/1989 | European Pat. Off. |
| 0345356 | 12/1989 | European Pat. Off. |
| 0457921 | 11/1991 | European Pat. Off. |
| 1-313488 | 12/1989 | Japan |
| WO9109041 | 6/1991 | PCT Int'l Appl. |

*Primary Examiner*—Cecilia Tsang
*Attorney, Agent, or Firm*—Austin R. Miller

[57] ABSTRACT

A platinum(II) complex represented by the general formula (A),

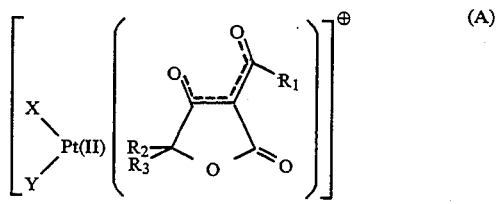

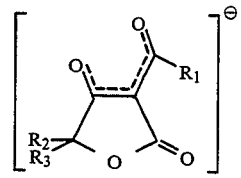

in which $R_1$ represents a hydrocarbon radical having 1 to 10 carbon atoms, $R_2$ and $R_3$ each represent a hydrogen atom or a hydrocarbon radical of 1 to 10 carbon atoms, or $R_2$ and $R_3$, together, may form $-(CH_2)_4-$ or $-(CH_2)_5-$, and X and Y each represent an ammonia molecule or a monodentate amine having 1 to 7 carbon atoms or X and Y, together, may form a bidentate diamine having 2 to 10 carbon atoms. The compounds are useful for treating a tumor.

13 Claims, 3 Drawing Sheets

PLATINUM(II) COMPLEX AND ANTITUMOR AGENT

BACKGROUND OF THE INVENTION

1. Field of the Invention

The present invention relates to a novel platinum complex, and to an antitumor agent and containing the platinum complex as an effective component.

2. Description of the Related Art

Extensive studies have been made of platinum complexes having an anti-tumor activity, and among those complexes, there are practically utilized cisdiamminedichloroplatinum(II) (Cisplatin: CDDP) and cisdiammine(1,1-cyclobutanedicarboxylato)platinum(II) (Carboplatin: CBDCA). Nevertheless, these complexes are defective in that the former has strong side effects and the latter has low anti-tumor activity.

SUMMARY OF THE INVENTION

A primary object of the present invention is to find compound having excellent anti-tumor activity and a low toxicity, and to provide same as an agent for treating a tumor.

Therefore, the present invention provides a novel platinum(II) complex represented by the following general formula (A),

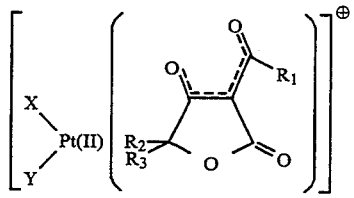

(A)

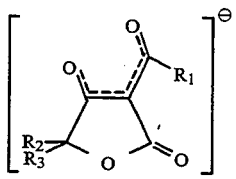

in which $R_1$ represents a hydrocarbon radical having 1 to 10 carbon atoms, $R_2$ and $R_3$ each represent a hydrogen atom or a hydrocarbon radical of 1 to 10 carbon atoms, or $R_2$ and $R_3$, together, may form —$(CH_2)_4$— or —$(CH_2)_5$—, and X and Y each represent an ammonia molecule or a monodentate amine having 1 to 7 carbon atoms or X and Y, together, may form a bidentate diamine having 2 to 10 carbon atoms, and an agent for treating a malignant tumor and containing the compound as an effective component.

DESCRIPTION OF THE PREFERRED EMBODIMENTS

Figure 1:
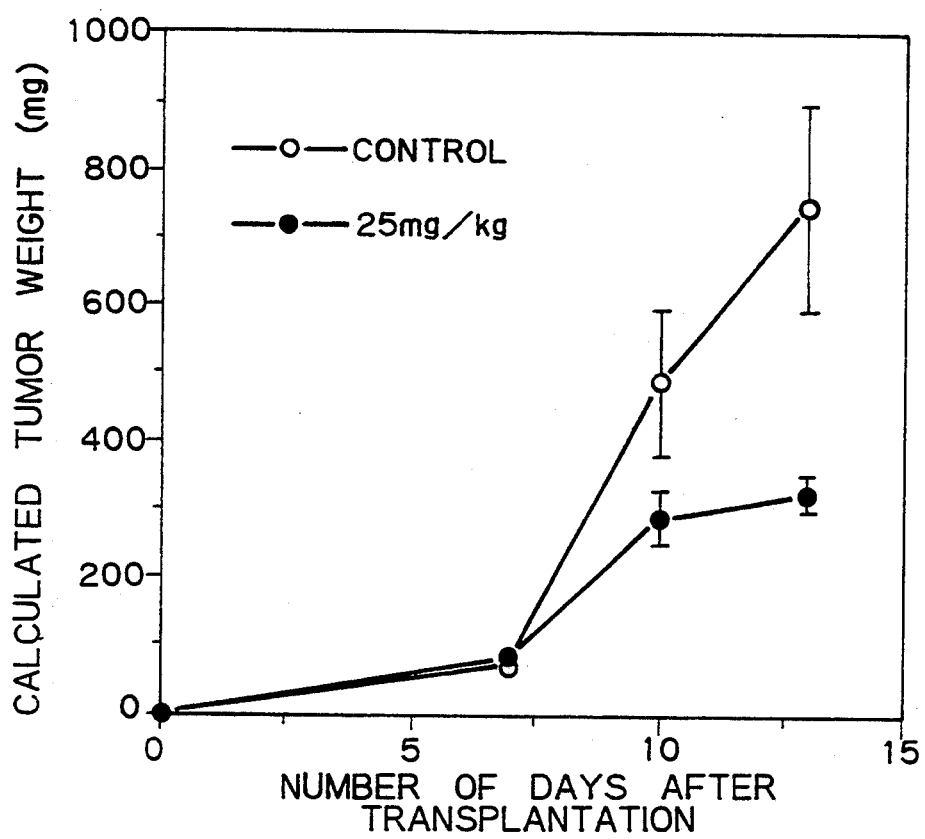
FIG. 1 is a graph showing the anti-tumor effect of Compound 1 obtained in Example 1 against colon-26 cells transplanted to a mouse.

The hydrocarbon radical for $R_1$, $R_2$ and $R_3$ is preferably alkyl, alkenyl, cycloalkyl, cycloalkyl-alkyl, aryl or aralkyl, although methyl is most preferred. The moiety,

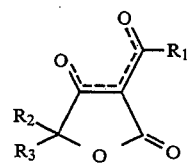

bonded to the platinum in formula (A) exhibits a tautomerism represented by the equation,

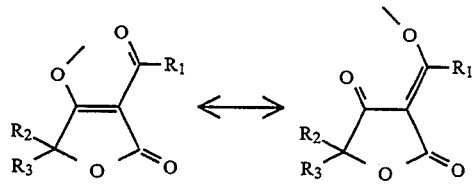

and chelates the platinum. The moiety,

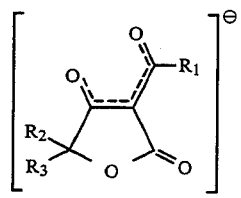

exhibits a tautomerism represented by the equation,

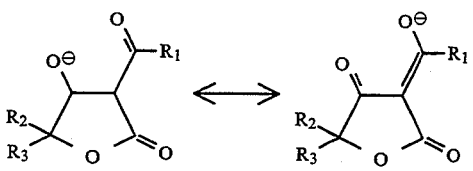

Where X and Y are an amine having one nitrogen atom, they are preferably an amine having a hydrocarbon radical of 1 to 10 carbon atoms where the hydrocarbon radical is preferably alkyl, alkenyl, cycloalkyl, cycloalkyl-alkyl, aryl or aralkyl. Examples of the amine include n-propylamine, iso-propylamine, n-butylamine, n-hexylamine, n-octylamine, cyclopropylamine, cyclobutylamine, cyclopentylamine, and cyclohexylamine.

Examples of the bidentate diamine formed by X and Y together include unsubstituted or substituted 1,2-diaminoethane, unsubstituted or substituted 1,3-diaminopropane, unsubstituted or substituted 1,4-diaminobutane and unsubstituted or substituted 2-aminomethylpyridine. The substituents on these diamines are preferably a radical composed of carbon and hydrogen atoms or of carbon, hydrogen and oxygen atoms and having 1 to 10 carbon atoms.

Examples of the substituted 1,2-diaminoethane include 1-methyl-1,2-diaminoethane, 1-ethyl-1,2- diaminoethane, 1-methyl-1-ethyl-1,2-diaminoethane, 3-phenyl-1,2-diaminopropane, N-methyl-1,2-diaminoethane, N-cyclopentyl-1,2-diaminoethane, N-cyclohexyl-1,2-diaminoethane, 1,2-diaminocyclopentane, 1,2-diaminocycloheptane, 1-(aminomethyl)-cyclopentylamine, 1-(aminomethyl)-cyclooctylamine, 3-aminopyrrolidine, 2 -(aminomethyl)-pyrrolidine, 2-(1-aminoethyl)-pyrrolidine, N-(1-aminoethyl)-pyrrolidine, N-(1-aminoethyl)-morpholine, 2-(aminomethyl)-aziridine, 2-(methylamino)-azetidine, and bicyclo[2,2,1]heptanediamine.

Examples of the substituted 1,3-diaminopropane include 2,2-dimethyl-1,3-diaminopropane, 2,2-diethyl-1,3-diaminopropane, 2-(n-butyl)-1,3-diaminopropane, 2-(n-hexyl)-1,3-diaminopropane, 2-methyl-2-methoxy-1,3-diaminopropane, 2,2-bis(hydroxymethyl)-1,3-diaminopropane, 2,2-bis(methoxyethyl)-1,3-diaminopropane, 1,1-bis(aminomethyl)-cyclopentane, 1,1-bis(aminomethyl)-cyclohexane, 4,4-bis(aminomethyl)-tetrahydropyran, 1,3-diaminocyclohexane, 2-(aminomethyl)-cyclopentane, 2-(aminomethyl)-cyclohexane, N-cyclohexyl-1,3-diaminopropane, and N-cyclopentyl-1,3-diaminopropane.

Examples of the substituted 1,4-diaminobutane include 1-methyl-1,4-diaminobutane, 2-methyl-1,4-diaminobutane, 1-ethyl-1,4-diaminobutane, 1,1-dimethyl-1,4-diaminobutane, 2,2-dimethyl-1,4-diaminobutane, 1,2-dimethyl-1,4-diaminobutane, and 1,3-dimethyl-1,4diaminobutane.

Examples of the substituted 2-aminomethylpyridine include 2-(1-aminoethyl)-pyridine, 2-(N-methylaminomethyl)-pyridine, and 2-(N-ethylaminoethyl)-pyridine.

Preferably, X and Y are an ammonia molecule or a molecule formed by X and Y together and represented by the following formula, $$NH_2-CH_2-\underset{\underset{R_5}{|}}{\overset{\overset{R_4}{|}}{C}}-CH_2-NH_2$$

in which $R_4$ and $R_5$ each represent a hydrogen atom or a hydrocarbon radical having 1 to 6 carbon atoms, or $R_4$ and $R_5$, together, form $-(CH_2)_l-$, (in which l is an integer of 3 to 5) or $-(CH_2)_2-O-(CH_2)_2-$.

The present inventors found that a complex can be synthesized in which one molecule of a deprotonated derivative of a five-membered ring compound (B) of the formula,

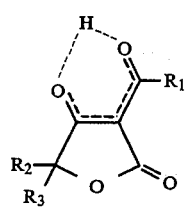

(B)

in which the compound (B) exhibits the tautomerism represented by the equation of

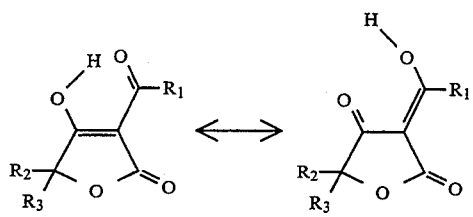

chelates the platinum (II), and another one molecule of the deprotonated derivative of the compound (B) in the form of anion is attached thereto to thereby form a complex. This complex is highly soluble in water and stable in an aqueous solution, and has a high anti-tumor activity.

The compound (A) may be synthesized by processes represented by the following equations (I) and (II).

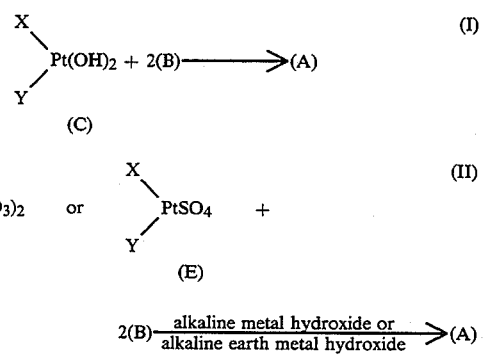

The compound (C) may be obtained by passing the compound (D) through a strong ion-exchange resin.

The compound (D) and (E), which are the materials for synthesizing the platinum complex of the present invention, can be obtained by known methods. For example, they can be easily obtained by treating a compound of the following formula (F) with silver nitrate or silver sulfate according to the procedure described in Journal of Pharmaceutical Sciences, 65, 315, (1976).

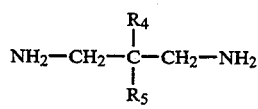

(F)

wherein X and Y are as defined above, and Hal represents halogen.

As the alkaline metal hydroxide used in the reaction (II), NaOH and KOH are preferred and as the alkaline earth metal hydroxide used therein, Ba(OH)$_2$ and Ca(OH)$_2$ are preferred. Two equivalents of the alkaline metal hydroxide or one equivalent of the alkaline earth metal hydroxide are preferably used.

The compound represented by the formula (B), which is another material, may be prepared by known methods, for example, as described in E. Benary, Berichte 42, 3912 (1909), or P. M. Booth et al., J. Chem. Soc. Perkin Trans, I, 121 (1987), or D. J. Agar et al., Tetrahedron Lett., 29, 4807 (1988).

Although the molar ratio of the compound (B) to the compounds (C), (D) and (E) is preferably about 2, no problem arises even if an excess amount of the compound (B) is used.

That the two moles of the deprotonated derivatives of the compound (B) are not identical is apparent from the fact that the proton signals with the same intensity are separately observed in NMR, and that the complex forms an ionic compound is known from the fact that one mole of the deprotonated derivative of B in the complex is easily replaced by another ion such as acetate ion. The complex of the present invention may be in the form of aquocomplex containing water and the aquocomplex is also included in the scope of the present invention.

The agent containing an effective amount of the platinum complex of the present invention may be clinically administered orally or parenterally. The agent may be in the form of tablet, sugar-coated tablet, pill, capsule, powder, troche, solution, suppository, injection and the like. The agent may be formulated using a pharmaceutically acceptable excipient. Examples of the pharmaceutically acceptable excipient include lactose, sucrose, glucose, sorbitol, xylitol, mannitol, potato starch, amylopectin, other various starches, cellulose derivatives such as carboxymethyl cellulose and hydroxyethyl cellulose, gelatin, magnesium stearate, polyvinyl alcohol, calcium stearate, polyethylene glycol wax, titanium dioxide, gum arabic, talc, vegetable oils such as olive oil, peanut oil and sesame oil, paraffin oil, neutral fat base, ethanol, propylene glycol, physiological saline, sterilized water, glycerin, coloring agent, flavoring agent, concentrating agent, stabilizer, isotonic agent, buffering agent and other pharmaceutically acceptable excipients.

The agent of the present invention preferably contains the platinum complex of the present invention in an amount of 0.001–85% by weight, most preferably 0.005–60% by weight.

Although the dosage of the agent varies mainly depending on the symptoms of a patient, it is 0.005–200 mg, preferably 0.01–50 mg, for an adult per body weight per day.

The invention will be further illustrated by the following non-limitative examples.

EXAMPLE 1

Compound 1

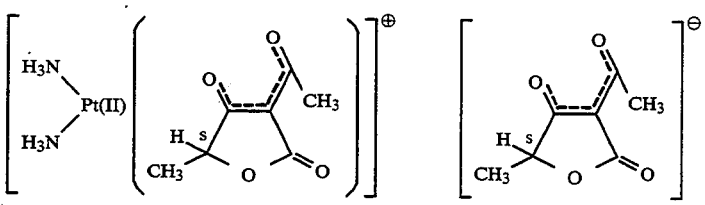

First, 12.49 g (80.0 mmol) of 3-acetyl-(5S)-5-methyl-tetrahydrofuran-2,4-dione is dissolved in 80 ml of water, 12.62 g (40.0 mmol) of barium hydroxide octahydrate is added to the solution and the mixture is stirred, and then 100 ml of a solution of 13.0 g (40 mmol) of sulfatodiamineplatinum(II) in water is added dropwise to the mixture, and the mixture is stirred at room temperature for 3 hours. Water-insoluble materials are filtered off using a membrane filter (0.45 μm), and the filtrate is concentrated using a rotary evaporator under a reduced pressure. Then 50 ml of ethanol is added to the residue, the solvent is distilled off under a reduced pressure, and thereafter, 50 ml of tetrahydrofuran is added to obtain a colorless solid material. The solid material is recovered by filtration and recrystallized from water to obtain 16.14 g (yield of 74.8%) of a colorless crystalline product.

The melting point, elementary analysis data and NMR spectrum data of the resulting complex are shown below.

Melting point: 230°–265° C. (decomposed)

| Elementary analysis: for $C_{14}H_{20}N_2O_8Pt$ | | | | |
| --- | --- | --- | --- | --- |
| | C | H | N | Pt |
| Calculated (%) | 31.17 | 3.74 | 5.19 | 36.17 |
| Found (%) | 31.03 | 3.80 | 5.09 | 36.27 |

$^1$H NMR (500 MHz, in $D_2O$, internal standard: $^1$H in $D_2O$)δ(ppm): 4.60 (1H, q), 3.71 (1H, q), 2.39 (3H, s), 2.38 (3H, s), 1.51 (3H, d), 1.43 (3H, d).

EXAMPLE 2

Compound 2

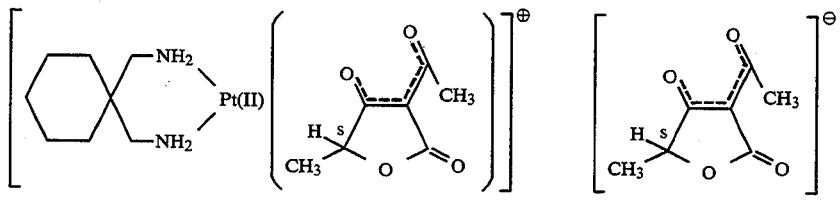

First, 1.26 g (4 mmol) of barium hydroxide octahydrate is added to 58 ml of an aqueous solution of 4 mmol of sulfato[1,1-bis(aminomethyl)-cyclohexane]platinum-(II), the mixture is stirred at room temperature for 1 hour in the dark, and then the reaction mixture is filtered to remove precipitates of barium sulfate. Thereafter, 1.25 g (8 mmol) of 3-acetyl-(5S)-5-methyltetrahydrofuran-2,4-dione is added to the filtrate, the mixture is stirred at room temperature for 2 hours in the dark, and then the reaction mixture is evaporated to dryness using a rotary evaporator. The residue is then dissolved in distilled water and the solution subjected to column chromatography using 150 ml of a packing (MCI-gel CHP20P, manufactured by Mitsubishi Kasei K.K.). Distilled water is passed through the column, and then the effluents by 30% methanol-distilled water are collected and evaporated to dryness using a rotary evaporator. The residue is added to tetrahydrofuran to be dissolved therein, and the solution is allowed to stand to form crystals. The crystalline product is recovered by filtration and vacuum dried to obtain the desired complex in a yield of 1.116 g.

The melting point, elementary analysis data and IR and NMR spectrum data of the resulting complex are shown below.

Melting point: 180–182° C. (decomposed)

| Elementary analysis: for $C_{22}H_{32}N_2O_8Pt$ | | | | |
| --- | --- | --- | --- | --- |
| | C | H | N | Pt |
| Calculated (%) | 40.80 | 4.98 | 4.33 | 30.12 |
| Found (%) | 40.71 | 4.92 | 4.30 | 30.15 |

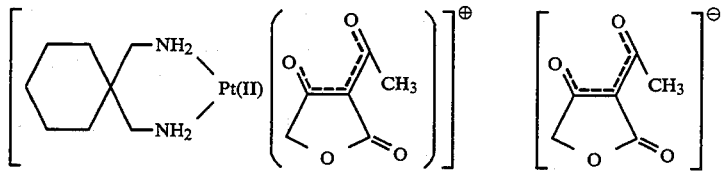

IR (KBr) (cm$^{-1}$): 3450, 3200, 3090, 2934, 1756, 1721, 1650, 1607, 1493, 1450, 1091, 1069, 1023, 969, 787

NMR (400 MHz, in D$_2$O) δ(ppm): 4.72 (1H, q), 4.52 (1H, q), 2.46 (4H, br, s), 2.32 (3H, s), 2.31 (3H, s), 1.45 (4H, br, m), 1.43 (3H, d), 1.40 (4H, br, m), 1.36 (3H, d)

EXAMPLE 3

Compound 3

First, 2.84 g (9 mmol) of barium hydroxide octahydrate is added to 132 ml of an aqueous solution of 9 mmol of sulfato[1,1-bis(aminomethyl)-cyclohexane]-platinum(II), the mixture is stirred at room temperature for 1 hour in the dark, and then the reaction mixture is filtered to remove precipitates of barium sulfate. Thereafter, 2.56 g (18 mmol) of 3-acetyltetrahydrofuran-2,4-dione is added to the filtrate, the mixture is stirred at room temperature for 4 hours in the dark, and then the reaction mixture is evaporated to dryness using a rotary evaporator. The residue is added to ethanol, and the formed precipitates are recovered by filtration. The precipitates are recrystallized from distilled water and vacuum dried to obtain colorless crystals of the desired complex in a yield of 3.416 g.

The melting point, elementary analysis data and IR and NMR spectrum data of the resulting complex are shown below.

Melting point: 147–150° C. (decomposed)

| Elementary analysis: for $C_{20}H_{28}N_2O_8Pt \cdot 0.9H_2O$ | | | | |
| --- | --- | --- | --- | --- |
| | C | H | N | Pt |
| Calculated (%) | 37.79 | 4.72 | 4.40 | 30.69 |

-continued

| Elementary analysis: for $C_{20}H_{28}N_2O_8Pt \cdot 0.9H_2O$ | | | | |
| --- | --- | --- | --- | --- |
| | C | H | N | Pt |
| Found (%) | 37.60 | 4.69 | 4.40 | 30.95 |

IR (KBr) (cm$^{-1}$): 3420, 3186, 3100, 2934, 2860, 1754, 1719, 1644, 1605, 1497, 1359, 1238, 1050, 1015, 926, 756, 661

NMR (500 MHz, in D$_2$O) δ(ppm): 4.56 (2H, s), 4.45 (2H, s), 2.53 (4H, d), 2.40 (3H, s), 2.38 (3H, s), 1.53 (6H, m), 1.46 (4H, m)

EXAMPLE 4

Compound 4

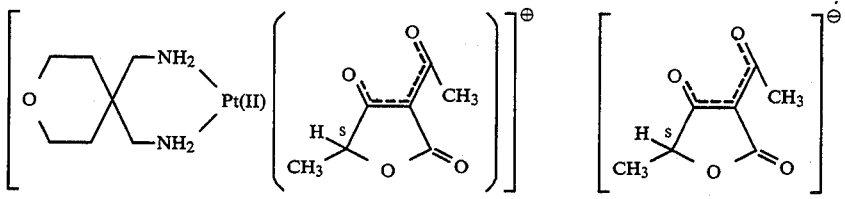

First, 1.26 (4 mmol) of barium hydroxide octahydrate is added to 70 ml of an aqueous solution of 4 mmol of sulfato[4,4-bis(aminomethyl)-tetrahydropyran]-platinum(II), the mixture is stirred at room temperature for 1 hour in the dark, and then the reaction mixture is filtered to remove precipitates of barium sulfate. Thereafter, 1.25 g (8 mmol) of 3-acetyl-(5S)-5-methyltetrahydrofuran-2,4-dione is added to the filtrate, the mixture is stirred at room temperature for 2 hours in the dark, and then the reaction mixture is evaporated to dryness using a rotary evaporator. The residue is dissolved in distilled water and the solution is subjected to column chromatography using 150 ml of a packing (MCI-gel CHP20P, manufactured by Mitsubishi Kasei K.K.). Distilled water is passed through the column, and then the effluents by 30% methanol-distilled water are collected and evaporated to dryness using a rotary evaporator. The residue is added to a small amount of methanol to be dissolved therein, and after the addition of tetrahydrofuran, the solution is allowed to stand to form crystals. The crystalline product is recovered by filtration and vacuum dried to obtain the desired complex in a yield of 1.851 g.

The melting point, elementary analysis data and IR and NMR spectrum data of the resulting complex are shown below. Signals originated from tetrahydrofuran are found in the NMR analysis data of the complex, which reveals that a minor amount of tetrahydrofuran is retained therein.

Melting point: 235° C (decomposed)

| Elementary analysis: for $C_{21}H_{30}N_2O_9Pt$ (0.25 $C_4H_8O$) | | | | |
|---|---|---|---|---|
|  | C | H | N | Pt |
| Calculated (%) | 39.58 | 4.83 | 4.20 | 29.22 |
| Found (%) | 39.41 | 4.79 | 4.32 | 29.26 |

IR (KBr) (cm$^{-1}$): 3450, 3092, 2964, 2864, 1748, 1715, 1650, 1603, 1491, 1456, 1093, 1069, 1029, 969, 787, 659

NMR (400 MHz, in $D_2O$) δ(ppm): 4.73 (1H, q), 4.52 (1H, q), 3.75 (5H, m, containing THF), 2.59 (4H, br, s), 2.32 (3H, s), 2.31 (3H, s), 1.87 (1H, m, THF), 1.60 (4H, br, q), 1.43 (3H, d), 1.36 (3H, d)

EXAMPLE 5
Compound 5

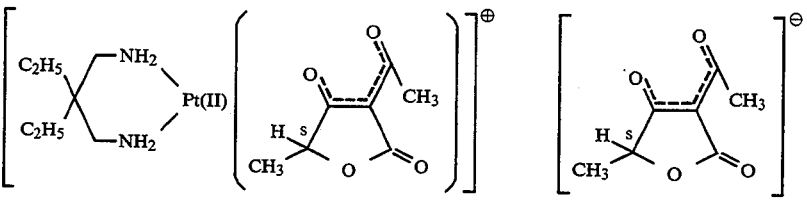

First, 1.28 g (8.20 mmol) of 3-acetyl-(5S)-5-methyltetrahydrofuran-2,4-dione is dissolved in 20 ml of water, 1.30 g (4.10 mmol) of barium hydroxide octahydrate is added to the solution, and the mixture is stirred. Thereafter, 120 ml of a solution of 1.73 g (4.10 mmol) of sulfato(2,2-diethyl-1,3-diaminopropane)platinum(II) in water is added dropwise to the mixture, and the mixture is stirred at room temperature for 12 hours. Water-insoluble materials are filtered off using a membrane filter (0.45 μm), and the filtrate is concentrated using a rotary evaporator under a reduced pressure, then 30 ml of ethanol is added to the residue, and the solvent is distilled off under a reduced pressure. The residue is then purified by column chromatography using a column packed with MCI-gel (efflux: methanol/water=3/7) to obtain 1.30 g (yield of 39.5%) of a pale yellow crystalline product.

The melting point, elementary analysis data and NMR spectrum data of the resulting complex are shown below.

Melting point: 189°–202° C. (decomposed)

| Elementary analysis: for $C_{21}H_{32}N_2O_8Pt$ | | | | |
|---|---|---|---|---|
|  | C | H | N | Pt |
| Calculated (%) | 39.69 | 5.07 | 4.41 | 30.69 |
| Found (%) | 39.39 | 5.20 | 4.29 | 30.40 |

$^1$H NMR (500 MHz, in $D_2O$) δ(ppm): 4.59 (1H, q), 3.80 (1H, q), 2.93 (4H, br, s,) 2.38 (6H, s), 1.93 (4H, m), 1.42 (6H, b), 1.23 (6H, m)

EXAMPLE 6
Compound 6

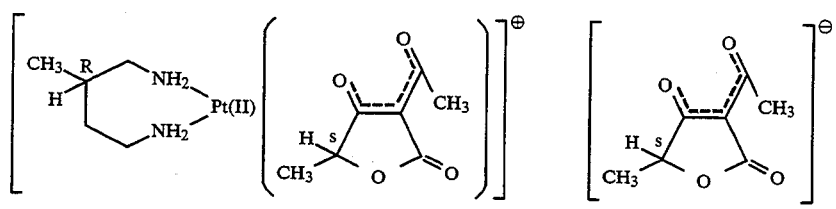

First, 4.68 g (30.0 mmol) of 3-acetyl-(5S)-5-methyltetrahydrofuran-2,4-dione is dissolved in 50 ml of water, 4.72 g (15.0 mmol) of barium hydroxide octahydrate is added to the solution, and the mixture is stirred at room temperature for 30 minutes. Then 150 ml of a 0.1 M aqueous solution of sulfato[(R)-2-methyl-1,4-butanediamine]platinum(II) is added dropwise to the mixture, and the mixture is immediately converted to become milky. The mixture is stirred for 12 hours, water-insoluble materials are filtered off using a membrane filter (0.45 μm) under a reduced pressure, the filtrate is evaporated to dryness under a reduced pressure, 50 ml of ethanol is added to the residue, and then the solvent is distilled off under a reduced pressure. After a further 50 ml of ethanol is added, insoluble materials are removed using a membrane filter (0.5 μm), and the mixture is concentrated under a reduced pressure. The residue is purified through a column chromatography using a column packed with MCI-gel CHP20P (developing solution: methanol/water=1/1) and is dried under a reduced pressure to obtain 5.39 g (yield of 59.1%) of a colorless amorphous product.

The melting point, elementary analysis data and NMR spectrum data of the resulting complex are shown below.

Melting point: about 253° C. (decomposed)

| Elementary analysis: for $C_{19}H_{28}N_2O_8Pt$ | | | | |
|---|---|---|---|---|
|  | C | H | N | Pt |
| Calculated (%) | 37.56 | 4.64 | 4.61 | 32.11 |
| Found (%) | 37.31 | 4.70 | 4.50 | 32.41 |

$^1$H NMR (400 MHz, in $D_2O$) δ(ppm): 1.40 (3H, d, J=6, 83 Hz), 1.45 (d, J=6, 83 Hz), 1.46 (d, J=7, 31 Hz), 1.46 (3H, m), 1.65 (3H, m), 2.33 (3H, s), 2.36 (3H, s), 2.51 (4H, m), 4.57 (1H, q, J=6, 83-Hz), 4.746 (q, J=6, 83 Hz), 4.751 (q, J=6, 83 Hz)

EXAMPLE 7

Mouse colon cancer colon-26 cells passed subcutaneously in BALB/c mice were delivered and punched, an appropriate amount of an MEM culture medium containing 0.05% of collagenase and 0.05% of hyaluronidase was added thereto, and the mixture was stirred at 30° C. for 1 hour. Then, the mixture was filtered by gauze under sterile conditions, and the cell liquid was adjusted to $4 \times 10^6$ cells/ml with Hanks' solution. The cell suspension was transplanted intracutaneously to BALB/c mice (male, 12 weeks old), each in an amount of 0.05 ml. From the 7th day after the transplantation, the above-mentioned Compound 1, 2 or 4 was administered intraperitoneally to the mice once a day for 3 days continuously. The anti-tumor effect was evaluated from the calculated tumor weight determined by the following equation.

Calculated tumor weight =

(long diameter) × (short diameter)$^2$ × 1/2

Figure 2:
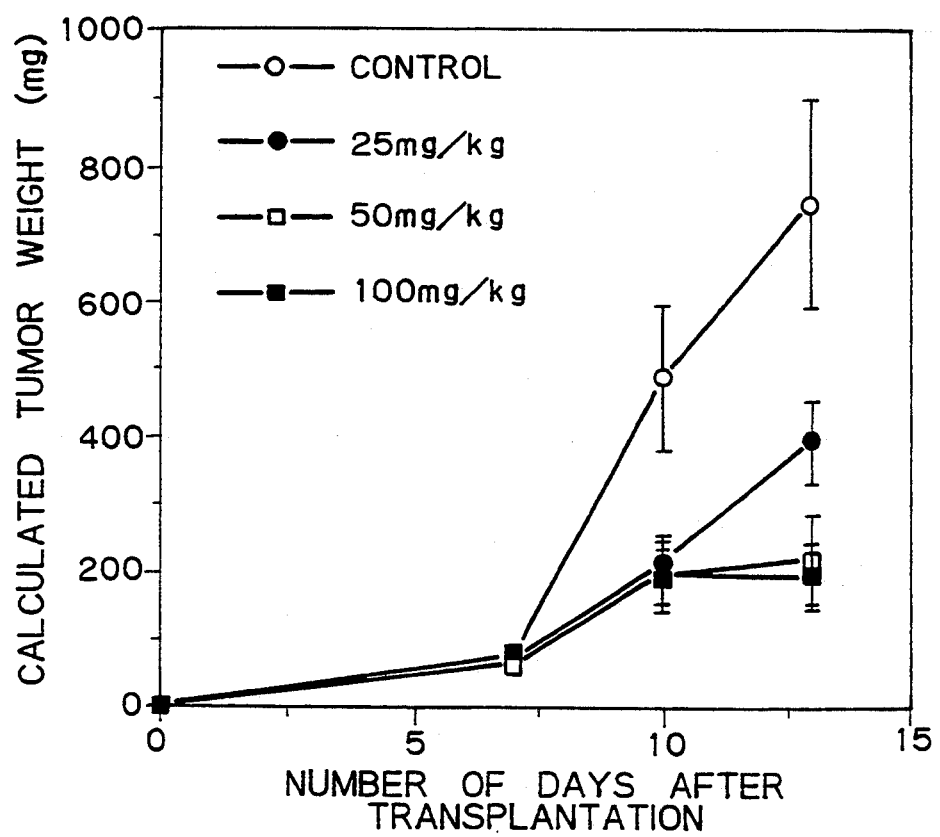
FIG. 2 is a graph showing the anti-tumor effect of Compound 2 obtained in Example 2 against colon-26 cells transplanted to a mouse; and, FIG. 3 is a graph showing the anti-tumor effect of Compound 4 obtained in Example 4 against colon-26 cells transplanted to a mouse.
Figure 3:
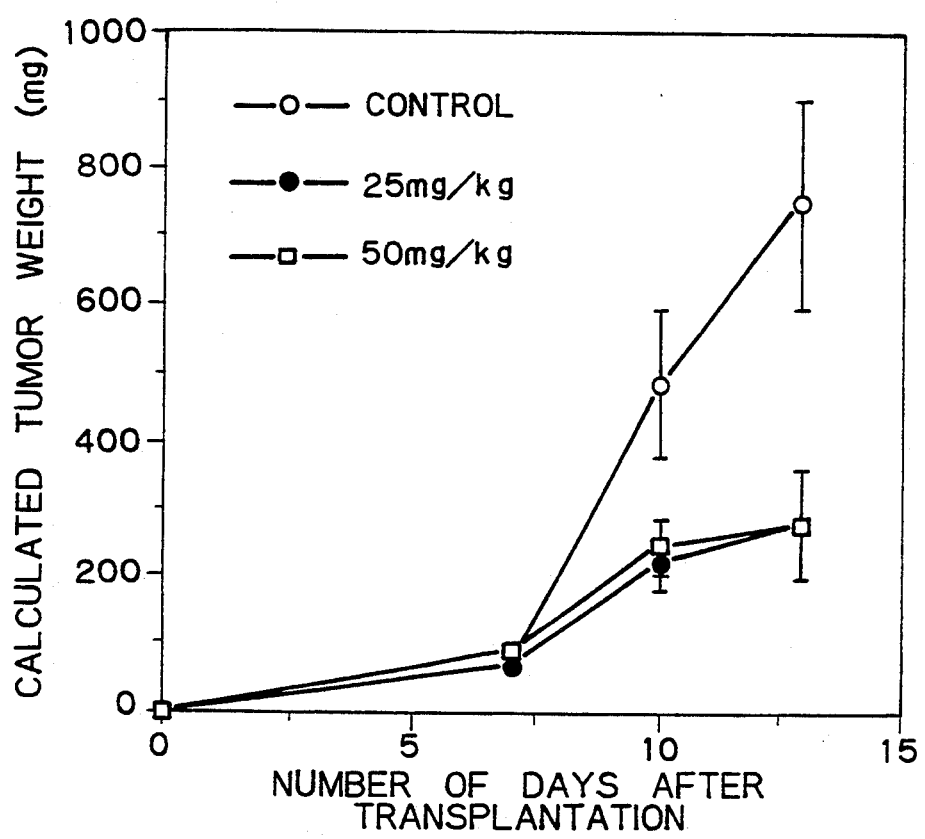

The results for Compounds 1, 2 and 4 are shown in FIGS. 1–3, respectively.

Compound 1 exhibited, as shown in FIG. 1, a tumor propagation inhibition of about 60% on the 13th day from the transplantation for the mouse group administered at a dose of 25 mg/kg. Compound 2 exhibited, as shown in FIG. 2, a tumor propagation inhibition of about 70% on the 13th day from the transplantation for the mouse groups administered at doses of 50 mg/kg and 100 mg/kg. Compound 4 exhibited, as shown in FIG. 3, a tumor propagation inhibition of about 60% on the 13th day from the transplantation for the mouse groups administered at doses of 25 mg/kg and 50 mg/kg.

From the above results, it is proved that the compounds according to the present invention have a strong anti-tumor effect against the mouse colon cancer colon-26 cells.

EXAMPLE 8

In this example, the anti-tumor activity of the exemplified compounds was evaluated.

$1 \times 10^5$ mouse leukemia L1210 cells passed in DBA/2 mice were transplanted in the abdominal cavities of CDF$_1$ mice (male, 6 weeks old, 6–10 animals/group). Counting from the day of transplantation, a compound to be tested was administered intraperitoneally to the mice on the 1st, 5th and 9th days, three times in total. Each of the tested compounds was used after being dissolved in distilled water for injection. The anti-tumor activity of the platinum complexes against the L1210 cell-planted mice was evaluated from the T/C value determined by the following equation.

$$T/C\ (\%) = \frac{\text{(average survival days of treated mice)}}{\text{(average survival days of control mice)}} \times 100$$

The data were obtained by observing the survival effect for the mice up to the 19th day from the transplantation.

The results are shown in Table 1 below.

TABLE 1

| Compound | Dose mg/kg | Average survival days | T/C % |
|---|---|---|---|
| Control | — | 8.2 ± 1.0 | 100 |
| Compound 2 | 6.3 | 9.7 ± 2.3 | 118 |
|  | 12.5 | 9.0 ± 1.4 | 110 |
|  | 25 | 10.3 ± 1.0 | 126 |
|  | 50 | 13.7 ± 3.0 | 167 |
|  | 100 | 9.8 ± 5.8 | 120 |
|  | 200 | 4.5 ± 1.4 | 55 |
| Compound 3 | 6.3 | 10.0 ± 1.3 | 122 |

TABLE 1-continued

| Compound | Dose mg/kg | Average survival days | T/C % |
|---|---|---|---|
|  | 12.5 | 11.3 ± 1.5 | 138 |
|  | 25 | 13.7 ± 4.4 | 167 |
|  | 50 | 16.3 ± 2.5 | 199 |
|  | 100 | 8.7 ± 0.5 | 106 |
|  | 200 | 4.0 ± 0.6 | 49 |

EXAMPLE 9

In this example, the acute toxicity of the exemplified compounds was tested while using CDDP as control.

A compound to be tested was intraperitoneally administered to Slc:ICR mice (male, 5 weeks old, animals/group). Each of the tested compounds was used after being dissolved in distilled water for injection. From the death rate after 14 days from the administration, the LD$_{50}$ value was determined according to Miller-Tainter method.

The results are shown in Table 2 below.

TABLE 2

| Compound | LD$_{50}$ (mg/kg) |
|---|---|
| Compound 1 | 74.1 |
| Compound 2 | 110.4 |
| Compound 3 | 142.1 |
| CDDP | 15.6 |

It is clear from the above that the compounds according to the present invention exhibit an excellent anti-tumor activity and a low toxicity, and therefore, are useful as an agent for treating a malignant tumor.

We claim:

1. A platinum(II) complex represented by the general formula (A),

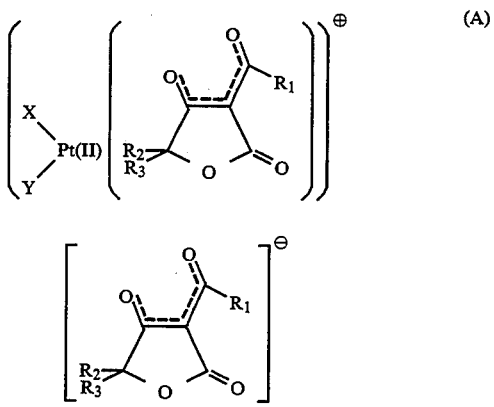

in which R$_1$ represents an aliphatic hydrocarbon radical having 1 to 10 carbon atoms, R$_2$ and R$_3$ each represent a hydrogen atom or an aliphatic hydrocarbon radical having 1 to 10 carbon atoms, or R$_2$ and R$_3$, together, may form —(CH$_2$)$_4$— or —(CH$_2$)$_5$—, and X and Y each represent an ammonia molecule or an aliphatic primary amine having 1 to 10 carbon atoms or X and Y, together, may form a diamine selected from the group consisting of unsubstituted 1,2-diaminoethane, 1,3-diaminopropane, 1,4-diaminobutane and 2-aminomethylpyridine, and 1,2-diaminoethane, 1,3-diaminopropane, 1,4-diaminobutane and 2-aminomethylpyridine substituted by an aliphatic hydrocarbon radical or aliphatic hydrocarbon ether radical having 1 to 10 carbon atoms.

2. A complex set forth in claim 1, wherein R₁ is alkyl having 1 to 10 carbon atoms, alkenyl having 2 to 10 carbon atoms, cycloalkyl having 3 to 10 carbon atoms, or cycloalkylalkyl having 4 to 10 carbon atoms and R₂ and R₃ are independently hydrogen, alkyl having 1 to 10 carbon atoms, alkenyl having 2 to 10 carbon atoms, cycloalkyl having 3 to 10 carbon atoms, or cycloalkylalkyl having 4 to 10 carbon atoms.

3. A complex as set forth in claim 1, wherein R₁ is methyl.

4. A complex as set forth in claim 1, wherein R₂ is hydrogen or methyl.

5. A complex as set forth in claim 1, wherein R₃ is hydrogen or methyl.

6. An agent for treating tumor comprising an effective amount of platinum(II) complex as defined in claim 1 in a pharmaceutically acceptable vehicle.

7. An agent as set forth in claim 6, wherein R₁ is methyl.

8. An agent as set forth in claim 6, wherein R₂ is hydrogen or methyl.

9. An agent as set forth in claim 6, wherein R₃ is hydrogen or methyl.

10. A complex as defined in claim 1 wherein said amine is selected from the group consisting of n-propylamine, iso-propylamine, n-butylamine, n-hexylamine, n-octylamine, cyclopropylamine, cyclobutylamine, cyclopentylamine and cyclohexylamine.

11. A complex as set forth in claim 1, wherein x and y each represent an ammonia molecule or an aliphatic primary amine having alkyl having 1 to 10 carbon atoms, alkenyl having 2 to 10 carbon atoms, cycloalkyl having 3 to 10 carbon atoms, or cycloalkylalkyl having 4 to 10 carbon atoms.

12. A platinum(II) complex represented by the general formula:

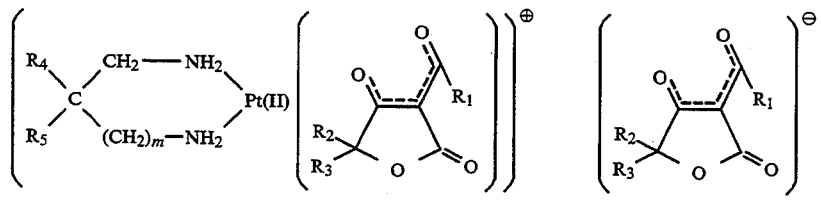

in which R₁ represents an aliphatic hydrocarbon radical having 1 to 10 carbon atoms, R₂ and R₃ each represent a hydrogen atom or an aliphatic hydrocarbon radical having 1 to 10 carbon atoms, or R₂ and R₃, together, form —(CH₂)₄— or (CH₂)₅—, R₄ and R₅ each represent a hydrogen atom or an aliphatic hydrocarbon radical or aliphatic hydrocarbon ether radical having 1 to 6 carbon atoms, the carbon atoms of the moiety

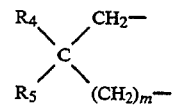

being not more than 10, or R₄ and R₅, together, form —(CH₂)ₗ—, in which l is an integer of 3 to 5, or —(CH₂)₂—O—(CH₂)₂—, and m is 1 or 2.

13. An agent for treating tumor comprising an antitumor effective amount of platinum(II) complex represented by the general formula:

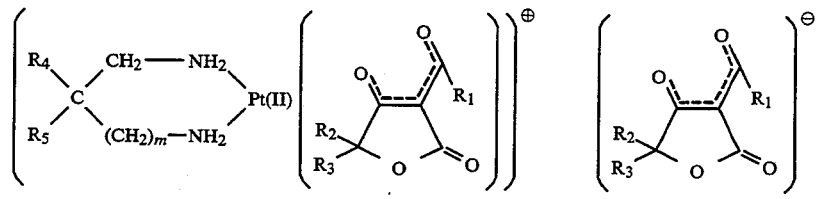

in which R₁ represents an aliphatic hydrocarbon radical having 1 to 10 carbon atoms, R₂ and R₃ each represent a hydrogen atom or an aliphatic hydrocarbon radical having 1 to 10 carbon atoms, or R₂ and R₃, together, form —(CH₂)₄— or —(CH₂)₅—, R₄ and R₅ each represent a hydrogen atom or an aliphatic hydrocarbon radical or aliphatic hydrocarbon ether radical having 1 to 6 carbon atoms, the carbon atoms or the moiety

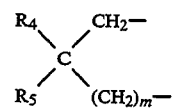

being not more than 10, or R₄ and R₅, together, form —(CH₂)ₗ—, in which l is an integer of 3 to 5, or —(CH₂)₂—O—(CH₂)₂—, and m is 1 or 2 is a pharmaceutically acceptable vehicle.

* * * * *

UNITED STATES PATENT AND TRADEMARK OFFICE
CERTIFICATE OF CORRECTION

PATENT NO. : 5,348,950
DATED : September 20, 1994
INVENTOR(S) : Go Hata et al

It is certified that error appears in the above-indentified patent and that said Letters Patent is hereby corrected as shown below:

Column 2, lines 40-48, please change the left side of the formula from:

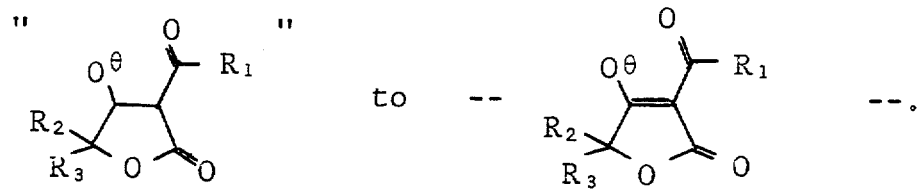

Column 3, bridging lines 22 and 23, please change "2-(aminomethyl)-cyclopentane" to
--2-(aminomethyl)-cyclopentylamine--; and
   line 23, please change "2-(aminomethyl)-cyclohexane" to --2-(aminomethyl)-cyclohexylamine--.

Column 12, line 16, after "old," insert --6--.

Signed and Sealed this

Thirteenth Day of June, 1995

Attest:

BRUCE LEHMAN

Attesting Officer     Commissioner of Patents and Trademarks